US007311737B2

(12) United States Patent
Metais et al.

(10) Patent No.: US 7,311,737 B2
(45) Date of Patent: Dec. 25, 2007

(54) SECONDARY PARA-PHENYLENEDIAMINE COMPOUNDS COMPRISING N-ALKYLFLUORINE, DYE COMPOSITIONS COMPRISING THEM AND PROCESSES OF DYEING THEREWITH

(75) Inventors: Eric Metais, St-Leu-la-Foret (FR); Stéphane Sabelle, Paris (FR)

(73) Assignee: L'Oreal, Paris (FR)

( * ) Notice: Subject to any disclaimer, the term of this patent is extended or adjusted under 35 U.S.C. 154(b) by 203 days.

(21) Appl. No.: 11/066,252

(22) Filed: Feb. 28, 2005

(65) Prior Publication Data

US 2006/0021157 A1    Feb. 2, 2006

Related U.S. Application Data

(60) Provisional application No. 60/569,651, filed on May 11, 2004.

(30) Foreign Application Priority Data

Feb. 27, 2004    (FR) .................................... 0402023

(51) Int. Cl.
    *A61K 7/13*    (2006.01)
(52) U.S. Cl. ....................... 8/405; 8/406; 8/410; 8/411; 8/412; 8/415; 8/416; 564/114
(58) Field of Classification Search .................. 8/405, 8/406, 408, 410, 411, 412, 415, 416; 564/114
    See application file for complete search history.

(56) References Cited

U.S. PATENT DOCUMENTS

| | | | |
|---|---|---|---|
| 2,516,106 A | 7/1950 | Dickey | |
| 3,355,454 A | 11/1967 | Klauke et al. | |
| 4,003,699 A | 1/1977 | Rose et al. | |
| 4,823,985 A | 4/1989 | Grollier et al. | |
| 5,061,289 A | 10/1991 | Clausen et al. | |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,708,151 A | 1/1998 | Möckli | |
| 5,766,576 A | 6/1998 | Lowe et al. | |
| 6,099,592 A | 8/2000 | Vidal et al. | |
| 6,284,003 B1 | 9/2001 | Rose et al. | |
| 6,338,741 B1 | 1/2002 | Vidal et al. | |
| 6,645,258 B2 | 11/2003 | Vidal et al. | |
| 6,730,789 B1 | 5/2004 | Birault et al. | |
| 2002/0050013 A1 | 5/2002 | Vidal et al. | |
| 2002/0053110 A1* | 5/2002 | Dias et al. ...................... | 8/405 |
| 2003/0019051 A9 | 1/2003 | Vidal et al. | |

FOREIGN PATENT DOCUMENTS

| | | |
|---|---|---|
| DE | 23 59 399 | 6/1975 |
| DE | 38 43 892 A1 | 6/1990 |
| DE | 41 33 957 A1 | 4/1993 |
| DE | 195 43 988 A1 | 5/1997 |
| EP | 0 532 039 B1 | 3/1993 |
| EP | 0 714 954 B1 | 6/1996 |
| EP | 0 770 375 B1 | 5/1997 |
| FR | 2 586 913 A1 | 3/1987 |
| FR | 2 733 749 A1 | 11/1996 |
| GB | 1 026 978 | 4/1966 |
| GB | 1 153 169 | 5/1969 |
| JP | 2-19576 | 1/1990 |
| JP | 5-163124 | 6/1993 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |
| WO | WO 01/16108 A2 | 3/2001 |

OTHER PUBLICATIONS

STIC Search Report dated Feb. 7, 2007.*
French Search Report for FR 0402023 dated Sep. 13, 2004.*
French Search Report for FR 0402023 (French priority application for the present application), dated Sep. 13, 2004, Examiner L. Can Amsterdam.
English language abstract of EP 0 770 375 B1, May 2, 1997.
English language abstract of JP 2-19576, Jan. 23, 1990.
English language abstract of JP 5-163124, Jun. 29, 1993.
Hiyoshizo Kotsuki et al., "High Pressure Organic Chemistry; XII. A Convenient Synthesis of Aromatic Amines from Activaed Aromatic Fluorides," Synthesis, Journal of Syntheic Organic Chemistry, pp. 1147-1148 (1990).
S. Massa, "Spiro-[4H-pyrrolo[1,2-a][1,4]benzodiazepine-4,4'-piperidine] Derivatives as Potential Nootropic Agents: A Simple One-Pot Synthesis," Synthetic Communications, vol. 20. No. 22, pp. 3537-3545 (1990).
Martin Steinman et al., "1-Polyfluroralkylbenzodiazepines," Journal of Medicinal Chemistry, vol. 16, No. 12, pp. 1354-1360 (1973).
Viacheslav A. Petrov, "Reaction of polyfluorinated imines with trifluoromethyltrimethylsilane. Direct synthesis of N-(perfluoro-t-butyl)amines," Tetrahedron Letters, No. 41, pp. 6959-6963 (2000).

* cited by examiner

*Primary Examiner*—Eisa Elhilo
(74) *Attorney, Agent, or Firm*—Finnegan, Henderson, Farabow, Garrett & Dunner, L.L.P.

(57) ABSTRACT

The present disclosure relates to novel secondary para-phenylenediamine compounds comprising N-alkylfluorine, to a process for preparing them, to a composition for dyeing keratin fibers, for example human keratin fibers such as the hair, comprising, in a medium that is suitable for dyeing, at least one secondary para-phenylenediamine compound comprising N-alkylfluorine as disclosed, to a process for dyeing keratin fibers with the disclosed compositions, and also to a dyeing "kit" comprising the dyeing compositions.

25 Claims, No Drawings

SECONDARY PARA-PHENYLENEDIAMINE COMPOUNDS COMPRISING N-ALKYLFLUORINE, DYE COMPOSITIONS COMPRISING THEM AND PROCESSES OF DYEING THEREWITH

This application claims benefit of U.S. Provisional Application No. 60/569,651, filed May 11, 2004, and French Patent Application No. 04/02023 filed Feb. 27, 2004, the contents of both of which are incorporated herein by reference.

The present disclosure relates to a novel family of secondary para-phenylenediamine compounds comprising N-alkylfluorine, to their preparation, to cosmetic compositions comprising them, and to the process of oxidation dyeing of keratin fibers therewith.

It is known practice to dye keratin fibers, such as human hair, with dye compositions comprising oxidation dye precursors, such as ortho- or para-phenylenediamines, ortho- or para-aminophenols, and heterocyclic compounds, which are generally referred to as oxidation bases. These oxidation bases are colorless or weakly colored compounds which, when combined with oxidizing products, may give rise to colored compounds by a process of oxidative condensation. It is also known that the shades obtained with oxidation bases may be varied by combining them with couplers or coloration modifiers, for example, coloration modifiers chosen from aromatic meta-diaminobenzenes, meta-aminophenols, meta-diphenols and certain heterocyclic compounds such as indole compounds. The variety of molecules used as oxidation bases and couplers can make it possible to obtain a wide range of colors.

The "permanent" coloration obtained by means of oxidation dyes, moreover, should be able to satisfy a certain number of requirements. Thus, the dyes should not have toxicological drawbacks, should allow shades of the desired intensity to be obtained, and/or should have good resistance to external agents such as light, bad weather, washing, permanent waving, perspiration and rubbing. The dyes may also allow white hairs to be covered and, lastly, the dye should ideally be as unselective as possible, i.e., allow the smallest possible differences in coloration to be produced over the entire length of the same keratin fiber, which is generally differently sensitized (i.e., damaged) between its end and its root.

It has been discovered, surprisingly and unexpectedly, that it is possible to obtain a novel family of secondary para-phenylenediamine compounds comprising N-alkylfluorine, which are capable of giving strong, aesthetic and sparingly selective colorations in varied shades, and which can show good resistance to the various attacking factors to which the fibers may be subjected. Accordingly, the present disclosure also relates to a process for preparing these secondary para-phenylenediamine compounds comprising N-alkylfluorine, and also to a process for oxidation dyeing the hair therewith.

Another aspect of the present disclosure relates to compositions for dyeing keratin fibers, for instance human keratin fibers such as the hair, comprising at least one secondary para-phenylenediamine compound comprising N-alkylfluorine, making it possible to obtain dyes that have the abovementioned benefits. In addition, these compositions may have a good toxicological profile.

Still another aspect of the present disclosure is a dyeing process comprising applying the compositions according to the present disclosure to keratin fibers, for instance human keratin fibers such as the hair, and a multi-compartment device or dyeing "kit" thereof.

The compositions of the present disclosure make it possible, for example, to obtain very powerful, sparingly selective and color-fast, for example light-fast, dyeing of keratin fibers, while at the same time avoiding the degradation of these fibers.

Other characteristics, aspects, and benefits of the present disclosure will emerge even more clearly upon reading the description and the non-limiting examples that follow.

The novel secondary para-phenylenediamine compounds comprising N-alkylfluorine according to the present disclosure are compounds of formula (I), and the addition salts thereof:

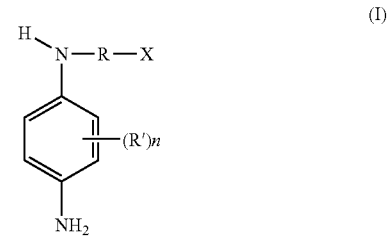

wherein:
X is a fluorine atom;
R is chosen from linear and branched $C_1$–$C_{10}$ alkylene radicals, which may be unsubstituted or substituted with at least one entity chosen from halogen atoms, and $C_1$–$C_{15}$ alkoxy, aryl, amino, mono($C_1$–$C_{15}$)alkylamino, di($C_1$–$C_{15}$)alkylamino, ($C_1$–$C_{15}$)alkylcarbonyl, carboxyl, amido, ($C_1$–$C_{15}$)alkoxycarbonyl, mono($C_1$–$C_{15}$)alkylaminocarbonyl, and di($C_1$–$C_{15}$)alkylaminocarbonyl radicals, wherein the alkylene radicals are optionally interrupted with at least one entity chosen from carbonyl functional groups and hetero atoms chosen from oxygen and nitrogen;
R' is chosen from a hydrogen atom, and $C_1$–$C_{15}$ alkyl, $C_1$–$C_{15}$ alkoxy, $C_1$–$C_{15}$ hydroxyalkoxy, ($C_1$–$C_{15}$)alkoxy($C_1$–$C_{15}$)alkyl, $C_1$–$C_{15}$ monohydroxyalkyl, and $C_1$–$C_{15}$ polyhydroxyalkyl radicals;
n is an integer ranging from 1 to 4;
with the proviso that the compounds of formula (I) are not chosen from
N-(3,3,3-trifluoropropyl)benzene-1,4-diamine,
N-(4,4,4-trifluorobutyl)benzene-1,4-diamine,
N-(5,5,5-trifluoroamyl)benzene-1,4-diamine,
N-(6,6,6-trifluorohexyl)benzene-1,4-diamine,
N-(2,2,2-trifluoroethyl)benzene-1,4-diamine, and
N-(2,2,2-trifluoroethyl)-2-methoxybenzene-1,4-diamine.

For example, the group R of formula (I) may be chosen from linear and branched $C_2$–$C_5$ alkylene radicals, which may be unsubstituted or substituted with at least one entity chosen from a fluorine atom, and $C_2$–$C_8$ alkoxy, aryl, amino, mono($C_2$–$C_8$)alkylamino, di($C_2$–$C_8$)alkylamino, ($C_2$–$C_8$)alkylcarbonyl, carboxyl, amido, ($C_2$–$C_8$)alkoxycarbonyl, mono($C_2$–$C_8$)alkylaminocarbonyl, and di($C_2$–$C_8$)alkylaminocarbonyl radicals, wherein the alkylene radicals are optionally interrupted with at least one entity chosen from carbonyl groups and hetero atoms chosen from oxygen and nitrogen, and the group R' of formula (I) may be chosen from a hydrogen atom, and $C_1$–$C_6$ alkyl, $C_1$–$C_8$ alkoxy, $C_1$–$C_8$ hydroxyalkoxy, ($C_1$–$C_8$)alkoxy($C_1$–$C_8$)alkyl, $C_1$–$C_8$ monohydroxyalkyl, and $C_1$–$C_8$ polyhydroxyalkyl radicals.

For further example, the compounds of general formula (I) may be chosen from the compounds of the following table:

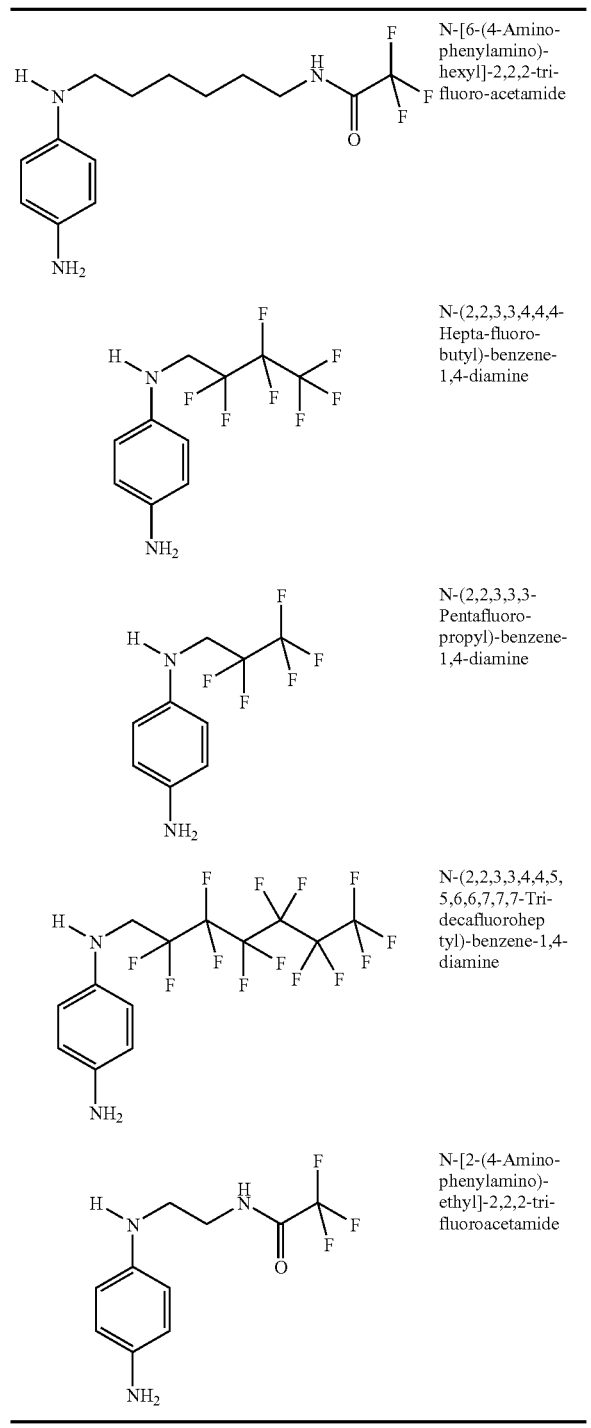

| | |
|---|---|
| | N-[6-(4-Amino-phenylamino)-hexyl]-2,2,2-tri-fluoro-acetamide |
| | N-(2,2,3,3,4,4,4-Hepta-fluoro-butyl)-benzene-1,4-diamine |
| | N-(2,2,3,3,3-Pentafluoro-propyl)-benzene-1,4-diamine |
| | N-(2,2,3,3,4,4,5,5,6,6,7,7,7-Tri-decafluorohep tyl)-benzene-1,4-diamine |
| | N-[2-(4-Amino-phenylamino)-ethyl]-2,2,2-tri-fluoroacetamide |

By way of non-limiting example, the addition salts that may be used for the oxidation bases and the couplers may be chosen from, for example, acid-addition salts, such as the hydrochlorides, hydrobromides, sulfates, citrates, succinates, tartrates, lactates, tosylates, benzenesulfonates, phosphates and acetates.

The compounds of formula (I) according to the present disclosure may be prepared, for instance, according to a method comprising:

- nucleophilic substitution of the halogen in the para position of the para-halonitrobenzene derivative with a primary amine of formula $R_1NH_2$ in the presence of a base;
- optional chemical modification of the radical $R_1$ into a radical R—X, R and X being defined as above;
- reduction of the nitro functional group of the compound obtained above into an amine functional group, to obtain the compound of formula (I).

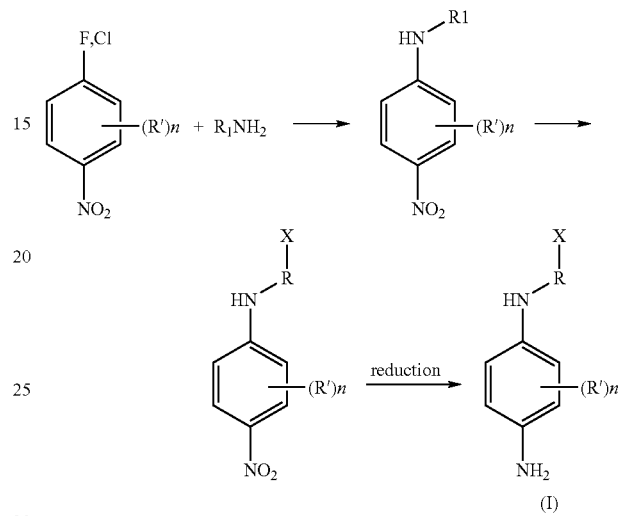

The first synthesis step is described in the scientific reviews *Synthesis* 1990 (12), 1147 –1148 and *Synth. Commun.* 1990, 20 (22), 3537–3545. The second step is a step of modification of the functional group present on the side chain of the amine. This type of reaction is standard and is described in general in the publication *Advanced Organic Chemistry*, 4$^{th}$ edition, 1992, J. MARCH, WILEY Interscience. The last step is a standard reduction step, for example by performing a hydrogenation reaction via heterogeneous catalysis in the presence of Pd/C, Pd(II)/C or Raney Ni, or alternatively by performing a reduction reaction with a metal, for example with zinc, iron, tin, etc. See, for example, *Advanced Organic Chemistry*, 4$^{th}$ edition, 1992, J. March, Wiley Interscience; *Reduction in Organic Chemistry*, 1983, M. Hudlicky, Ellis Honwood series Chemical Science.

The present disclosure thus also relates to processes for preparing the secondary para-phenylenediamine compounds comprising N-alkylfluorine and having formula (I), comprising reducing the corresponding nitro compound, wherein the corresponding nitro compound is the compound of formula (I) in which the amino group in the para position to the NHRX group is replaced with a nitro group.

The present disclosure also relates to the use of the compound of formula (I) and the addition salts thereof for the oxidation dyeing of the hair:

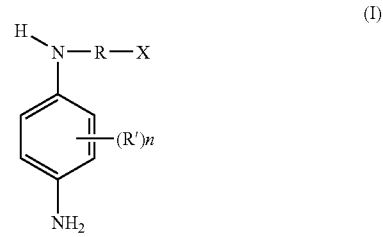

wherein:

X is a fluorine atom;

R is chosen from linear and branched $C_1$–$C_{10}$ alkylene radicals, which are unsubstituted or substituted with at least one entity chosen from halogen atoms, and a $C_1$–$C_{15}$ alkoxy, aryl, amino, mono($C_1$–$C_{15}$)alkylamino, di($C_1$–$C_{15}$)alkylamino, ($C_1$–$C_{15}$)alkylcarbonyl, carboxyl, amido, ($C_1$–$C_{15}$) alkoxycarbonyl, mono($C_1$–$C_{15}$)alkylaminocarbonyl, and di($C_1$–$C_{15}$)alkylaminocarbonyl radicals, wherein the alkylene radicals are optionally interrupted with at least one entity chosen from carbonyl functional groups and hetero atoms chosen from oxygen and nitrogen;

R' is chosen from a hydrogen atom, and $C_1$–$C_{15}$ alkyl, $C_1$–$C_{15}$ alkoxy, $C_1$–$C_{15}$ hydroxyalkoxy, ($C_1$–$C_{15}$)alkoxy ($C_1$–$C_{15}$)alkyl, $C_1$–$C_{15}$ monohydroxyalkyl, and $C_1$–$C_{15}$ polyhydroxyalkyl radicals;

n is an integer ranging from 1 to 4.

The present disclosure also relates to a cosmetic composition for dyeing keratin fibers, for instance human keratin fibers such as the hair, comprising, in a medium that is suitable for dyeing, at least one compound of formula (I) and/or the addition salts thereof:

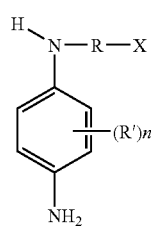

(I)

wherein:

X is a fluorine atom;

R is chosen from linear and branched $C_1$–$C_{10}$ alkylene radicals, which are unsubstituted or substituted with at least one entity chosen from halogen atoms and $C_1$–$C_{15}$ alkoxy, aryl, amino, mono($C_1$–$C_{15}$)alkylamino, di($C_1$–$C_{15}$)alkylamino, ($C_1$–$C_{15}$)alkylcarbonyl, carboxyl, amido, ($C_1$–$C_{15}$) alkoxycarbonyl, mono($C_1$–$C_{15}$)alkylaminocarbonyl, and di($C_1$–$C_{15}$)alkylaminocarbonyl radicals, wherein the alkylene radicals are optionally interrupted with at least one entity chosen from carbonyl functional groups and hetero atoms chosen from oxygen and nitrogen;

R' is chosen from a hydrogen atom, and $C_1$–$C_{15}$ alkyl, $C_1$–$C_{15}$ alkoxy, $C_1$–$C_{15}$ hydroxyalkoxy, ($C_1$–$C_{15}$)alkoxy ($C_1$–$C_{15}$)alkyl, $C_1$–$C_{15}$ monohydroxyalkyl and $C_1$–$C_{15}$ polyhydroxyalkyl radicals; and n is an integer ranging from 1 to 4.

For example, the group R of formula (I) may be chosen from linear and branched $C_2$–$C_5$ alkylene radicals, which are unsubstituted or substituted with at least one entity chosen from a fluorine atom, and $C_2$–$C_8$ alkoxy, aryl, amino, mono ($C_2$–$C_8$)alkylamino, di($C_2$–$C_8$)alkylamino, ($C_2$–$C_8$)alkylcarbonyl, carboxyl, amido, ($C_2$–$C_8$)alkoxycarbonyl, mono ($C_2$–$C_8$)alkylaminocarbonyl, and di($C_2$–$C_8$) alkylaminocarbonyl radicals, these alkylene radicals possibly being interrupted with at least one entity chosen from carbonyl groups and hetero atoms chosen from oxygen and nitrogen, and the group R' of formula (I) may be chosen from a hydrogen atom, and $C_1$–$C_6$ alkyl, $C_1$–$C_8$ alkoxy, $C_1$–$C_8$ hydroxyalkoxy, ($C_1$–$C_8$)alkoxy($C_1$–$C_8$)alkyl, $C_1$–$C_8$ monohydroxyalkyl and $C_1$–$C_8$ polyhydroxyalkyl radicals.

For further example, the composition may comprise at least one compound of formula (I) chosen from:

N-(2,2,2-trifluoroethyl)benzene-1,4-diamine;

N-(2,2,3,3,4,4,4-heptafluorobutyl)benzene-1,4-diamine;

N-(2,2,3,3,3-pentafluoropropyl)benzene-1,4-diamine;

N-(2,2,3,3,4,4,5,5,6,6,7,7,7-tridecafluoroheptyl)benzene-1, 4-diamine;

N-[2-(4-aminophenylamino)ethyl]-2,2,2-trifluoroacetamide; and

N-[6-(4-aminophenylamino)hexyl]-2,2,2-trifluoroacetamide.

For instance, the at least one compound of formula (I) can be present in the composition in an amount ranging from 0.0001% to 20%, such as from 0.005% to 6% by weight, relative to the total weight of the composition.

The medium that is suitable for dyeing, for example, can consist of water, or can comprise a mixture of water and at least one organic solvent, for instance branched or unbranched $C_1$–$C_4$ lower alcohols, such as ethanol and isopropanol; polyols and polyol ethers, for instance 2-butoxyethanol, propylene glycol, propylene glycol monomethyl ether, diethylene glycol monomethyl ether and monoethyl ether, glycerol, and also aromatic alcohols, for instance benzyl alcohol or phenoxyethanol, and mixtures thereof.

The at least one organic solvent, when present, can be present in an amount ranging from 1% to 40% by weight, such as ranging from 5% to 30% by weight, relative to the total weight of the dye composition.

For example, the cosmetic composition can further comprise at least one cosmetic adjuvant chosen from antioxidants, penetrating agents, sequestering agents, fragrances, buffers, dispersants, surfactants, conditioning agents, film-forming agents, polymers, ceramides, preserving agents, nacreous agents, opacifiers, vitamins and provitamins.

The at least one adjuvant, when present, can be present in an amount for each adjuvant ranging from 0.01% to 20% by weight, relative to the weight of the composition.

The composition according to the present disclosure can also comprise, for instance, at least one oxidation coupler.

Among the oxidation couplers that may be used, non-limiting mention can be made of meta-phenylenediamines, meta-aminophenols, meta-diphenols, naphthalene-based couplers, heterocyclic couplers, and the addition salts thereof.

Non-limiting examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene (or resorcinol), 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2, 6-dimethoxypyridine, 1-N-(β-hydroxyethyl)amino-3,4-methylenedioxybenzene, 2,6-bis(β-hydroxyethylamino) toluene, and the addition salts thereof.

The at least one oxidation coupler, when present, can be present in an amount ranging from 0.0001% to 20%, for example ranging from 0.005% to 6% by weight, relative to the total weight of the composition.

The composition according to the present disclosure may also comprise at least one additional oxidation base other than the compound of formula (I).

The additional oxidation bases may be chosen from, for example, para-phenylenediamines, bis(phenyl)alkylenediamines, para-aminophenols, ortho-amino phenols, heterocyclic bases, and the addition salts thereof.

Among the para-phenylenediamines that may be used, non-limiting mention may be made, by way of example, of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, 6-(4-aminophenylamino)hexan-1-ol, and the acid addition salts thereof.

Among the para-phenylenediamines mentioned above, further non-limiting mention may be made of para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine and the acid addition salts thereof.

Among the bis(phenyl)alkylenediamines that may be used, mention may be made, by way of non-limiting example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl) tetramethylenediamine, N,N'-bis(4-methylaminophenyl) tetramethylenediamine, N,N'-bis(ethyl)-N,N'-bis(4'-amino-3'-methyl-phenyl)ethylenediamine,1,8-bis(2,5-diaminophenoxy)-3,6-dioxaoctane, and the acid addition salts thereof.

Among the para-aminophenols that may be used, mention may be made, by way of non-limiting example, of para-aminophenol, 4-amino-3-methylphenol, 4-amino-3-fluorophenol, 4-amino-2-chlorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, 4-amino-2,6-dichlorophenol, 4-amino-6[((5'-amino-2'-hydroxy-3'-methyl)phenyl)methyl]-2-methylphenol, bis(5'-amino-2'-hydroxy)phenylmethane, and the acid addition salts thereof.

Among the ortho-aminophenols that may be used, mention may be made, by way of non-limiting example, of 2-aminophenol, 2-amino-5-methylphenol, 2-amino-6-methylphenol, 5-acetamido-2-aminophenol, and the acid addition salts thereof.

Among the heterocyclic bases that may be used, mention may be made, by way of non-limiting example, of pyridine derivatives, pyrimidine derivatives and pyrazole derivatives.

Among the pyridine derivatives, non-limiting mention may be made of the compounds described, for example, in British Patent Nos. GB 1 026 978 and GB 1 153 196, as well as 2,5-diaminopyridine, 2-(4-methoxyphenyl)amino-3-aminopyridine, 3,4-diaminopyridine, and the acid addition salts thereof. Other pyridine oxidation bases that are useful in the present invention are the 3-aminopyrazolo[1,5-a]pyridine oxidation bases and the addition salts thereof described, for example, in French Patent Application No. FR 2 801 308. Non-limiting examples that may be mentioned include pyrazolo[1,5-a]pyrid-3-ylamine; 2-acetylaminopyrazolo[1,5-a]pyrid-3-ylamine; 2-morpholin-4-ylpyrazolo[1,5-a]pyrid-3-ylamine; 3-aminopyrazolo[1,5-a]pyridin-2-carboxylic acid; 2-methoxypyrazolo[1,5-a]pyrid-3-ylamine; (3-aminopyrazolo[1,5-a]pyrid-7-yl)methanol; 2-(3-aminopyrazolo[1,5-a]pyrid-5-yl)ethanol; 2-(3-aminopyrazolo[1,5-a]pyrid-7-yl) ethanol; (3-aminopyrazolo[1,5-a]pyrid-2-yl) methanol; 3,6-diaminopyrazolo[1,5-a]pyridine; 3,4-diaminopyrazolo[1,5-a]pyridine; pyrazolo[1,5-a]pyrid-3,7-diamine; 7-morpholin-4-ylpyrazolo[1,5-a]pyrid-3-ylamine; pyrazolo[1,5-a]pyrid-3,5-diamine; 5-morpholin-4-ylpyrazolo[1,5-a]pyrid-3-ylamine; 2-[(3-aminopyrazolo[1,5-a]pyrid-5-yl)-(2-hydroxyethyl)amino]ethanol; 2-[(3-aminopyrazolo[1,5-a]pyrid-7-yl)-(2-hydroxyethyl)amino]ethanol; 3-aminopyrazolo[1,5-a]pyrid-5-ol; 3-aminopyrazolo[1,5-a]pyrid-4-ol; 3-aminopyrazolo[1,5-a]-pyridine-6-ol; 3-aminopyrazolo[1,5-a]pyrid-7-ol; and the acid addition salts thereof.

Among the pyrimidine derivatives that may be used, non-limiting mention may be made of the compounds described, for example, in German Patent No. DE 2 359 399; Japanese Patent Nos. JP 88-169 571 and JP 05 63 124; European Patent No. EP 0 770 375, and International Patent Application No. WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof and the tautomeric forms thereof, when a tautomeric equilibrium exists.

Among the pyrazole derivatives that may be used, non-limiting mention may be made of the compounds described in German Patent Nos. DE 3 843 892, and DE 4 133 957, and International Patent Application Nos. WO 94/08969 and WO 94/08970, French Patent Application No. FR-A-2,733,749, and German Patent Application No. DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4- methylaminopyrazole, 3,5-diamino-4-(β-hydroxyethyl)amino-1-methylpyrazole, and the addition salts thereof.

The at least one oxidation base other than those of formula (I) can be present in an amount, for example, ranging from 0.0001% to 20%, such as from 0.005% to 6% by weight, relative to the total weight of the composition.

The addition salts that may be used for the oxidation bases and couplers as described herein, for instance, can be chosen from, for example, the addition salts with an acid such as the hydrochlorides, hydrobromides, sulfates, citrates, succinates, tartrates, lactates, tosylates, benzenesulfonates, phosphates and acetates.

The dye composition in accordance with the present disclosure may also comprise at least one direct dye, which may be chosen from, for instance, neutral, acidic and cationic nitrobenzene dyes; neutral, acidic and cationic azo direct dyes; neutral, acidic and cationic quinone, such as anthraquinone direct dyes, azine direct dyes, methine, azomethine, triarylmethane and indoamine direct dyes; and natural direct dyes. For example, the composition according to the present disclosure may comprise at least one dye chosen from cationic direct dyes and natural direct dyes.

Among the cationic direct dyes that may be used according to the present disclosure, non-limiting mention may be made of the cationic azo direct dyes described in International Patent Application Nos. WO 95/15144 and WO 95/01772, and European Patent Application No. EP 714 954.

Among these compounds, further non-limiting mention may be made, for example, of the following dyes:
1,3-dimethyl-2-[[4-(dimethylamino)phenyl]azo]-1H-imidazolium chloride,
1,3-dimethyl-2-[(4-aminophenyl)azo]-1H-imidazolium chloride, and
1-methyl-4-[(methylphenylhydrazono)methyl]pyridinium methyl sulfate.

Among the natural direct dyes that may be used according to the present disclosure, non-limiting mention may be made of lawsone, juglone, alizarin, purpurin, carminic acid, kermesic acid, purpurogallin, protocatechaldehyde, indigo, isatin, curcumin, spinulosin, and apigenidin. It is also possible to use extracts or decoctions comprising these natural dyes, such as henna-based poultices or extracts.

The at least one direct dye, when present in the composition, can be present in an amount ranging from 0.001% to 20% by weight, for instance ranging from 0.005% to 10% by weight, relative to the total weight of the ready-to-use composition.

A ready-to-use dye composition of the present disclosure can be obtained by adding at least one oxidizing agent conventionally used for the oxidation dyeing of keratin fibers such as, for example, hydrogen peroxide, urea peroxide, alkali metal bromates, persalts such as perborates and persulfates, peracids and oxidase enzymes, among which, non-limiting mention may be made of peroxidases, two-electron oxidoreductases such as uricases, and four-electron oxygenases, for instance laccases. In one embodiment of the present disclosure, hydrogen peroxide is used.

Needless to say, a person skilled in the art will take care to select the adjuvant(s), precursor(s), additional oxidation dye(s), oxidation coupler(s) and direct dye(s) such that the beneficial properties intrinsically associated with the oxidation dye composition in accordance with the present disclosure are not, or are not substantially, adversely affected by the envisaged addition(s).

The pH of the dye composition in accordance with the present disclosure can range from 3 to 12, for example, from 5 to 11. It may be adjusted to the desired value using acidifying or basifying agents usually used in the dyeing of keratin fibers, or alternatively using standard buffer systems.

Among the acidifying agents that may be mentioned, by way of non-limiting example, are mineral or organic acids other than carboxylic diacids, for instance hydrochloric acid, orthophosphoric acid, sulfuric acid, carboxylic acids, for instance acetic acid, tartaric acid, citric acid and lactic acid, and sulfonic acids.

Among the basifying agents that may be mentioned, by way of non-limiting example, are aqueous ammonia, alkali metal carbonates, alkanolamines such as monoethanolamine, diethanolamine and triethanolamine and also derivatives thereof, sodium hydroxide, potassium hydroxide and the compounds of formula (II):

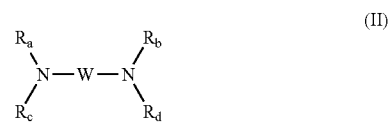

wherein W is a propylene residue optionally substituted with a hydroxyl group or a $C_1$–$C_4$ alkyl radical; $R_a$, $R_b$, $R_c$ and $R_d$, which may be identical or different, are chosen from hydrogen atoms, and $C_1$–$C_4$ alkyl and $C_1$–$C_4$ hydroxyalkyl radicals.

The dye composition according to the present disclosure may be in various forms, such as in the form of liquids, creams or gels, or in any other form that is suitable for dyeing keratin fibers, such as human hair.

Another aspect of the present disclosure relates to a process in which the composition as defined above is applied to the fibers and the color is developed using an oxidizing agent. The color may be developed at acidic, neutral or alkaline pH. The at least one oxidizing agent may be added to the composition as disclosed herein just at the time of use. It may be used starting with an oxidizing composition comprising it, which is applied simultaneously with or sequentially to the composition of the invention.

According to one embodiment of the present disclosure, the composition as disclosed herein is mixed, for example, at the time of use, with a composition comprising, in a medium that is suitable for dyeing, at least one oxidizing agent, this oxidizing agent being present in an amount that is sufficient to develop a coloration. The mixture obtained is then applied to the keratin fibers. After a period of action time ranging from 3 minutes to 50 minutes, for instance from 5 minutes to 30 minutes, the keratin fibers are rinsed, washed with shampoo, rinsed again and then dried.

The oxidizing composition may comprise various adjuvants conventionally used in hair dye compositions and as defined above.

The pH of the oxidizing composition comprising the oxidizing agent is such that, after mixing with the dye composition, the pH of the resulting ready-to-use composition applied to the keratin fibers can range, for example, from 3 to 12, such as from 5 to 11. It may be adjusted to the desired value by means of acidifying or basifying agents usually used in the dyeing of keratin fibers and as defined above.

The ready-to-use composition that is finally applied to the keratin fibers may be in various forms, such as in the form of liquids, creams or gels, or in any other form that is suitable for dyeing keratin fibers, for instance human keratin fibers such as human hair.

The present disclosure also relates to the use of the cosmetic composition as disclosed herein comprising, in a medium that is suitable for dyeing, at least one compound of formula (I) for dyeing fibers, for instance human keratin fibers such as the hair.

Another aspect of the present disclosure is a multi-compartment device or dyeing "kit," in which at least one first compartment comprises at least one dye composition as defined above, and at least one second compartment comprises at least one oxidizing composition. This kit may be equipped with a device for applying the desired mixture to the hair, such as the devices described in French Patent No. FR 2 586 913. Using this kit, it is possible to dye keratin fibers via a process that includes mixing a dye composition as disclosed herein with at least one oxidizing agent as defined above, and applying the mixture obtained, also called a ready-to-use dye composition, to the keratin fibers for a time that is sufficient to develop the desired coloration.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. The examples that follow serve to illustrate the invention without, however, being limiting in nature.

EXAMPLES

Example 1

Synthesis of N-[2-(4-amino-2-methylphenylamino) ethyl-2,2,2-trifluoroacetamide (2)

Step 1: Preparation of N-[2-(4-nitro-2-methylphenylamino)ethyl]-2,2,2-trifluoroacetamide (1)

1.55 g (0.01 mol) of 2-fluoro-5-nitrotoluene, 2.65 g (0.025 mol) of sodium carbonate, 2.11 g (0.011 mol) of 2-(trifluoroacetamido)ethylamine hydrochloride and 10 ml of N-methyl-pyrrolidone were introduced into a three-necked flask under nitrogen. The mixture was heated to 90° C. After reaction for 48 hours, the reaction mixture was cooled and 30 ml of distilled water were then added slowly with vigorous stirring. A yellow precipitate appeared. This precipitate was filtered off, washed several times with water and then with pentane, and dried under vacuum. 1.9 g of expected nitro derivative (1) were obtained in the form of a yellow powder.

Step 2: Preparation of N-[2-(4-amino-2-methylphenylamino)ethyl]-2,2,2-trifluoroacetamide (2)

1.7 g of nitro derivative (1) prepared above and about 80 ml of methanol were introduced into a 200 ml autoclave (hydrogenator) equipped with a magnetic stirrer. The solution obtained was degassed with nitrogen. 0.2 g of palladium-on-charcoal (5% humidity, comprising 50% water) was added thereto. The reaction mixture was stirred, after flushing once with hydrogen, and hydrogen was then introduced therein at a pressure of about 5 bar. After reaction for 4 hours, the reactor was purged with nitrogen. The reaction mixture was filtered quickly through Celite under a gentle pressure of nitrogen. The filtrate: was recovered in a pre-cooled solution of methanol comprising about 3 equivalents of hydrogen chloride gas. The resulting mixture was rinsed several times with methanol under a stream of nitrogen. The concentrated solution thus obtained was then treated with ether. The product obtained, in the form of a pale pink paste, was stirred and then rinsed several times with acetonitrile and ether under nitrogen. 1.65 g of expected product (2) were isolated in the form of a slightly pink white powder. The proton and 13C NMR spectra and the microanalyses were in accordance with the expected structure of the product.

Example 2

Synthesis of N-4-(2,2,2-trifluoro)ethyl-2-methylbenzene-1,4-diamine (4)

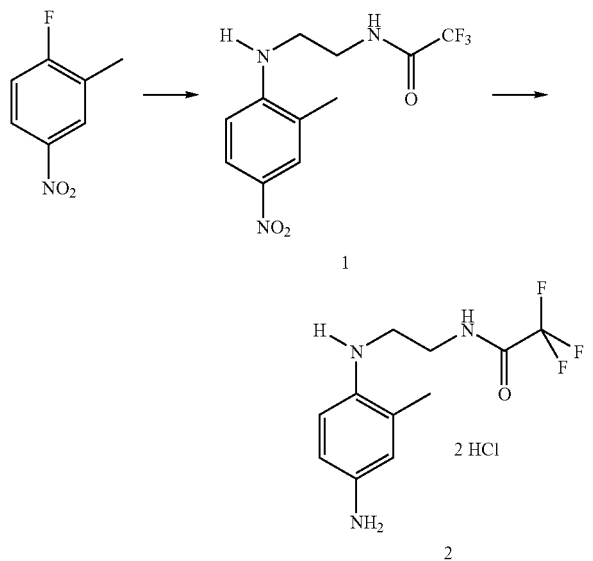

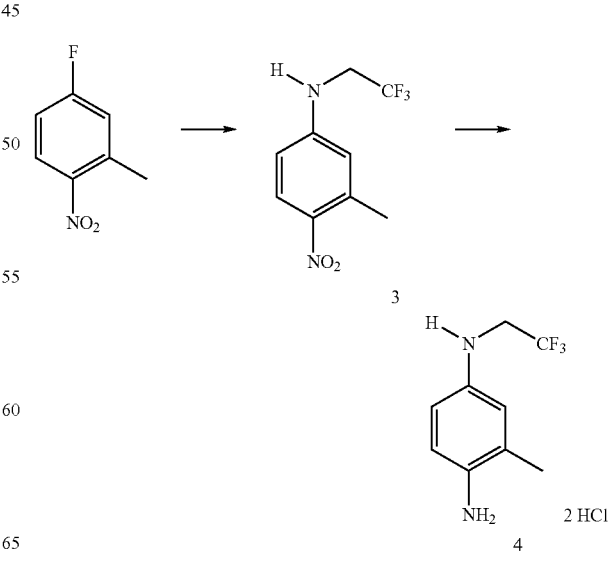

Step 1: Preparation of N-4-(2,2,2-trifluoroethyl-2-methylbenzene-4-nitro-1-amine (3)

1.55 g (0.01 mol) of 5-fluoro-2-nitrotoluene, 1.3 g (0.0122 mol) of sodium carbonate, 1.18 g (0.012 mol) of 2,2,2-trifluoroethylamine and 10 ml of N-methyl-pyrrolidone were introduced into a three-necked flask under nitrogen. The mixture was heated to 100° C. After reaction for 6 days, the reaction mixture was cooled and 30 ml of distilled water were then added slowly with vigorous stirring. The nitro derivative appeared in the form of a yellow semi-solid and was extracted with dichloromethane and then purified on a column of silica, eluting with ⅔ ethyl acetate/heptane. 0.3 g of expected nitro derivative (3) was obtained in the form of a dark yellow solid. The proton and $^{13}C$ NMR spectra were in accordance with the expected structure of the product.

Step 2: Preparation of N-4-(2,2,2-trifluoro)ethyl-2-methylbenzene-1,4-diamine (4)

The N-4-(2,2,2-trifluoroethyl-2-methylbenzene-4-nitro-1-amine (3) obtained above was reduced with a boiling zinc/ammonium chloride/water/ethanol mixture. The corresponding amine was isolated in the form of the dihydrochloride.

The proton NMR and mass spectra were in accordance with the expected structure of the product.

Example 3

Synthesis of N-(2,2,3,3,3-pentafluoropropyl)benzene-1,4-diamine dihydrochloride (6)

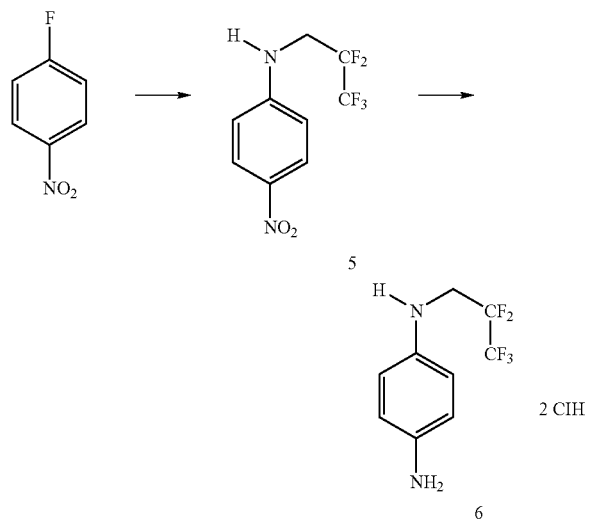

Step 1: Preparation of N-(4-nitrophenyl)-N-(2,2,3,3,3-pentafluoropropyl)amine (5)

1.55 g (0.01 mol) of 1-fluoro-4-nitrobenzene, 1.3 g (0.0122 mol) of sodium carbonate, 2.4 g (0.0225 mol) of 2,2,3,3,3-pentafluoropropylamine hydrochloride and 10 ml of N-methyl-pyrrolidone were introduced into a three-necked flask under nitrogen. The mixture was heated to 100° C. After reaction for 6 days, the reaction mixture was cooled and 30 ml of distilled water were then added slowly with vigorous stirring. The nitro derivative appeared in the form of a brown semi-solid, and was extracted with dichloromethane. The organic phase was evaporated under vacuum until all of the N-methyl-pyrrolidone had been removed. Distilled water was added to the brown oil obtained. A dark yellow precipitate appeared. This precipitate was filtered off, washed several times with water and then with pentane, and then dried under vacuum. 0.5 g of expected nitro derivative was obtained.

Step 2: Preparation of N-(2,2,3,3,3-pentafluoropropyl)benzene-1,4-diamine dihydrochloride (6)

The N-(4-nitrophenyl)-N-(2,2,3,3,3-pentafluoropropyl)amine (5) obtained above was reduced with a boiling zinc/ammonium chloride/water/ethanol mixture. The corresponding amine was isolated in the form of the dihydrochloride.

The proton NMR and mass spectra were in accordance with the expected structure of the product.

What is claimed is:

1. A secondary para-phenylenediamine compound chosen from compounds of formula (I), and the addition salts thereof:

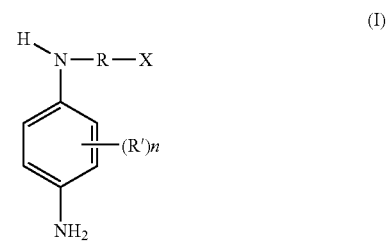

wherein:

X is a fluorine atom;

R is chosen from linear and branched $C_1$–$C_{10}$ alkylene radicals, which are unsubstituted or substituted with at least one entity chosen from halogen atoms, and $C_1$–$C_{15}$ alkoxy, aryl, amino, mono($C_1$–$C_{15}$)alkylamino, di($C_1$–$C_{15}$)alkylamino, ($C_1$–$C_{15}$)alkylcarbonyl, carboxyl, amido, ($C_1$–$C_{15}$)alkoxycarbonyl, mono($C_1$–$C_{15}$) alkylaminocarbonyl, and di($C_1$–$C_{15}$)alkylaminocarbonyl radicals, wherein the alkylene radicals are optionally interrupted with at least one entity chosen from carbonyl functional groups and hetero atoms chosen from oxygen and nitrogen;

R' is chosen from a hydrogen atom, and $C_1$–$C_{15}$ alkyl, $C_1$–$C_{15}$ alkoxy, $C_1$–$C_{15}$ hydroxyalkoxy, ($C_1$–$C_{15}$) alkoxy($C_1$–$C_{15}$)alkyl, $C_1$–$C_{15}$ monohydroxyalkyl, and $C_1$–$C_{15}$ polyhydroxyalkyl radicals;

n is an integer ranging from 1 to 4;

with the proviso that the compounds of formula (I) are not chosen from

N-(3,3,3-trifluoropropyl)benzene-1,4-diamine,
N-(4,4,4-trifluorobutyl)benzene-1,4-diamine,
N-(5,5,5-trifluoroamyl)benzene-1,4-diamine,
N-(6,6,6-trifluorohexyl)benzene-1,4-diamine,
N-(2,2,2-trifluoroethyl)benzene-1,4-diamine, and
N-(2,2,2-trifluoroethyl)-2-methoxybenzene-1,4-diamine.

2. The secondary para-phenylenediamine compound according to claim 1, wherein R is chosen from linear and branched $C_2$–$C_5$ alkylene radicals, which may be unsubstituted or substituted with at least one entity chosen from a fluorine atom, and $C_2$–$C_8$ alkoxy, aryl, amino, mono($C_2$–$C_8$) alkylamino, di($C_2$–$C_8$)alkylamino, ($C_2$–$C_8$)alkylcarbonyl, carboxyl, amido, ($C_2$–$C_8$)alkoxycarbonyl, mono($C_2$–$C_8$) alkylaminocarbonyl, and di($C_2$–$C_8$)alkylaminocarbonyl radicals, wherein the alkylene radicals are optionally interrupted with at least one entity chosen from carbonyl groups and hetero atoms chosen from oxygen and nitrogen.

3. The secondary para-phenylenediamine compound according to claim 1, wherein R' is chosen from a hydrogen atom, and $C_1$–$C_6$ alkyl, $C_1$–$C_8$ alkoxy, $C_1$–$C_8$ hydroxyalkoxy, ($C_1$–$C_8$)alkoxy($C_1$–$C_8$)alkyl, $C_1$–$C_8$ monohydroxyalkyl and $C_1$–$C_8$ polyhydroxyalkyl radicals.

4. The secondary para-phenylenediamine compound according to claim 1, wherein the compound of formula (I) is chosen from:
N-[6-(4-aminophenylamino)hexyl]-2,2,2-trifluoroacetamide;
N-(2,2,3,3,4,4,4-heptafluorobutyl)benzene-1,4-diamine;
N-(2,2,3,3,3-pentafluoropropyl)benzene-1,4-diamine;
N-(2,2,3,3,4,4,5,5,6,6,7,7,7-tridecafluoroheptyl)benzene-1,4-diamine; and
N-[2-(4-aminophenylamino)ethyl]-2,2,2-trifluoroacetamide.

5. The secondary para-phenylenediamine compound according to claim 1, wherein the addition salts of the secondary para-phenylenediamine compounds of formula (I) are chosen from hydrochlorides, hydrobromides, sulfates, citrates, succinates, tartrates, lactates, tosylates, benzenesulfonates, phosphates and acetates.

6. A process for preparing secondary para-phenylenediamine compounds of formula (I):

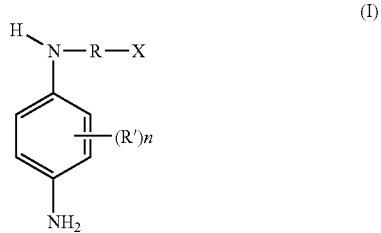

(I)

wherein:
X is a fluorine atom;
R is chosen from linear and branched $C_1$–$C_{10}$ alkylene radicals, which are unsubstituted or substituted with at least one entity chosen from halogen atoms, and $C_1$–$C_{15}$ alkoxy, aryl, amino, mono($C_1$–$C_{15}$)alkylamino, di($C_1$–$C_{15}$)alkylamino, ($C_1$–$C_{15}$)alkylcarbonyl, carboxyl, amido, ($C_1$–$C_{15}$)alkoxycarbonyl, mono($C_1$–$C_{15}$) alkylaminocarbonyl, and di($C_1$–$C_{15}$)alkylaminocarbonyl radicals, wherein the alkylene radicals are optionally interrupted with at least one entity chosen from carbonyl functional groups and hetero atoms chosen from oxygen and nitrogen;
R' is chosen from a hydrogen atom, and $C_1$–$C_{15}$ alkyl, $C_1$–$C_{15}$ alkoxy, $C_1$–$C_{15}$ hydroxyalkoxy, ($C_1$–$C_{15}$) alkoxy($C_1$–$C_{15}$)alkyl, $C_1$–$C_{15}$ monohydroxyalkyl, and $C_1$–$C_{15}$ polyhydroxyalkyl radicals;
n is an integer ranging from 1 to 4;
with the proviso that the compounds of formula (I) are not chosen from
N-(3,3,3-trifluoropropyl)benzene-1,4-diamine,
N-(4,4,4-trifluorobutyl)benzene-1,4-diamine,
N-(5,5,5-trifluoroamyl)benzene-1,4-diamine,
N-(6,6,6-trifluorohexyl)benzene-1,4-diamine,
N-(2,2,2-trifluoroethyl)benzene-1,4-diamine, and
N-(2,2,2-trifluoroethyl)-2-methoxybenzene-1,4-diamine,
said process comprising reducing a nitro compound corresponding to the secondary para-phenylenediamine compound of formula (I), wherein said nitro compound is the compound of formula (I) in which the amino group in the para position to the NHRX group is replaced with a nitro group.

7. A cosmetic composition for dyeing keratin fibers, comprising, in a medium that is suitable for dyeing, at least one compound chosen from those of formula (I) and the addition salts thereof:

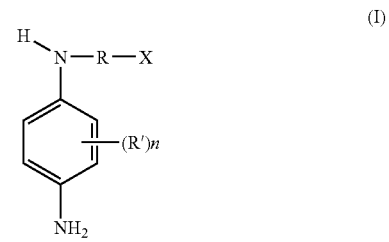

(I)

wherein:
X is a fluorine atom;
R is chosen from linear and branched $C_1$–$C_{10}$ alkylene radicals, which are unsubstituted or substituted with at least one entity chosen from halogens, and $C_1$–$C_{15}$ alkoxy, aryl, amino, mono($C_1$–$C_{15}$)alkylamino, di($C_1$–$C_{15}$)alkylamino, ($C_1$–$C_{15}$)alkylcarbonyl, carboxyl, amido, ($C_1$–$C_{15}$)alkoxycarbonyl, mono($C_1$–$C_{15}$) alkylaminocarbonyl, and di($C_1$–$C_{15}$)alkylaminocarbonyl radicals, wherein the alkylene radicals are optionally interrupted with at least one entity chosen from carbonyl functional groups and hetero atoms chosen from oxygen and nitrogen;
R' is chosen from a hydrogen atom, and $C_1$–$C_{15}$ alkyl, $C_1$–$C_{15}$ alkoxy, $C_1$–$C_{15}$ hydroxyalkoxy, ($C_1$–$C_{15}$) alkoxy($C_1$–$C_{15}$)alkyl, $C_1$–$C_{15}$ monohydroxyalkyl, and $C_1$–$C_{15}$ polyhydroxyalkyl radicals; and
n is an integer ranging from 1 to 4.

8. The cosmetic composition according to claim 7, wherein R is chosen from linear and branched $C_2$–$C_5$ alkylene radicals, which are unsubstituted or substituted with at least one entity chosen from a fluorine atom and $C_2$–$C_8$ alkoxy, aryl, amino, mono($C_2$–$C_8$)alkylamino, di($C_2$–$C_8$)alkylamino, ($C_2$–$C_8$)alkylcarbonyl, carboxyl, amido, ($C_2$–$C_8$)alkoxycarbonyl, mono($C_2$–$C_8$)alkylaminocarbonyl, and di($C_2$–$C_8$)alkylaminocarbonyl radicals, wherein the alkylene radicals are optionally interrupted with at least one entity chosen from carbonyl groups and hetero atoms chosen from oxygen and nitrogen.

9. The cosmetic composition according to claim 7, wherein R' is chosen from a hydrogen atom, and $C_1$–$C_6$ alkyl, $C_1$–$C_8$ alkoxy, $C_1$–$C_8$ hydroxyalkoxy, ($C_1$–$C_8$)alkoxy ($C_{1-8}$)alkyl, $C_1$–$C_8$ monohydroxyalkyl, and $C_1$–$C_8$ polyhydroxyalkyl radicals.

10. The cosmetic composition according to claim 7, wherein the at least one compound chosen from those of formula (I) and the addition salts thereof is chosen from:
N-(2,2,2-trifluoroethyl)benzene-1,4-diamine;
N-(2,2,3,3,4,4,4-heptafluorobutyl)benzene-1,4-diamine;

N-(2,2,3,3,3-pentafluoropropyl)benzene-1,4-diamine;

N-(2,2,3,3,4,4,5,5,6,6,7,7,7-tridecafluoroheptyl)benzene-1,4-diamine;

N-[2-(4-aminophenylamino)ethyl]-2,2,2-trifluoroacetamide;

N-[6-(4-aminophenylamino)hexyl]-2,2,2-trifluoroacetamide; and the addition salts thereof.

11. The cosmetic composition according to claim 7, wherein the at least one compound of formula (I) is present in an amount ranging from 0.0001% to 20% by weight, relative to the total weight of the composition.

12. The cosmetic composition according to claim 11, wherein the at least one compound of formula (I) is present in an amount ranging from 0.005% to 6% by weight, relative to the total weight of the composition.

13. The cosmetic composition according to claim 7, wherein the medium that is suitable for dyeing consists of water, or comprises a mixture of water and of at least one organic solvent chosen from branched and unbranched $C_1$–$C_4$ lower alcohols, polyols, polyol ethers, and aromatic alcohols.

14. The cosmetic composition according to claim 7, further comprising at least one cosmetic adjuvant chosen from antioxidants, penetrating agents, sequestering agents, fragrances, buffers, dispersants, surfactants, conditioning agents, film-forming agents, polymers, ceramides, preserving agents, nacreous agents, opacifiers, vitamins and provitamins.

15. The cosmetic composition according to claim 14, wherein the at least one cosmetic adjuvant is present in an amount, for each adjuvant, ranging from 0.01% to 20% by weight, relative to the total weight of the composition.

16. The cosmetic composition according to claim 7, further comprising at least one oxidation coupler chosen from meta-phenylenediamines, meta-aminophenols, meta-diphenols, naphthalene-based couplers, heterocyclic couplers, and the addition salts thereof.

17. The cosmetic composition according to claim 16, wherein the at least one coupler is present in an amount ranging from 0.0001% to 20% by weight, relative to the total weight of the composition.

18. The cosmetic composition according to claim 7, further comprising at least one additional oxidation base other than those of formula (I), chosen from para-phenylenediamines, bis(phenyl)alkylenediamines, para-aminophenols, ortho-aminophenols, heterocyclic bases, and the addition salts thereof.

19. The cosmetic composition according to claim 18, wherein the at least one additional oxidation base is present in an amount ranging from 0.0001% to 20% by weight, relative to the total weight of the composition.

20. The cosmetic composition according to claim 7, further comprising at least one direct dye chosen from natural and cationic direct dyes.

21. A process for dyeing keratin fibers, comprising
applying to the keratin fibers, for a period of time sufficient to develop a desired coloration, a composition comprising, in a medium suitable for dyeing, at least one compound chosen from those of formula (I) and the addition salts thereof:

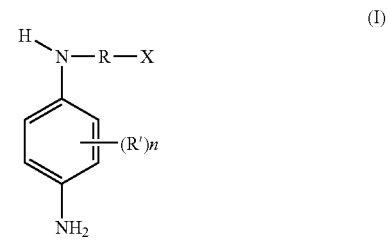

wherein:
X is a fluorine atom;
R is chosen from linear and branched $C_1$–$C_{10}$ alkylene radicals, which are unsubstituted or substituted with at least one entity chosen from halogens, and $C_1$–$C_{15}$ alkoxy, aryl, amino, mono($C_1$–$C_{15}$)alkylamino, di($C_1$–$C_{15}$)alkylamino, ($C_1$–$C_{15}$)alkylcarbonyl, carboxyl, amido, ($C_1$–$C_{15}$)alkoxycarbonyl, mono($C_1$–$C_{15}$)alkylaminocarbonyl, and di($C_1$–$C_{15}$)alkylaminocarbonyl radicals, wherein the alkylene radicals are optionally interrupted with at least one entity chosen from carbonyl functional groups and hetero atoms chosen from oxygen and nitrogen;
R' is chosen from a hydrogen atom, and $C_1$–$C_{15}$ alkyl, $C_1$–$C_{15}$ alkoxy, $C_1$–$C_{15}$ hydroxyalkoxy, ($C_1$–$C_{15}$)alkoxy($C_1$–$C_{15}$)alkyl, $C_1$–$C_{15}$ monohydroxyalkyl, and $C_1$–$C_{15}$ polyhydroxyalkyl radicals; and
n is an integer ranging from 1 to 4.

22. The process according to claim 21, wherein said keratin fibers are human hair.

23. A ready-to-use cosmetic composition, comprising, in a medium that is suitable for dyeing keratin fibers,
at least one oxidizing agent chosen from hydrogen peroxide, urea peroxide, alkali metal bromates, persalts, peracids and oxidase enzymes, and
at least one compound chosen from those of formula (I) and the addition salts thereof:

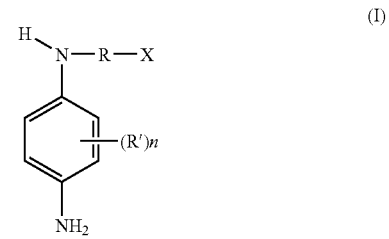

wherein:
X is a fluorine atom;
R is chosen from linear and branched $C_1$–$C_{10}$ alkylene radicals, which are unsubstituted or substituted with at least one entity chosen from halogens, and $C_1$–$C_{15}$ alkoxy, aryl, amino, mono($C_1$–$C_{15}$)alkylamino, di($C_1$–$C_{15}$)alkylamino, ($C_1$–$C_{15}$)alkylcarbonyl, carboxyl, amido, ($C_1$–$C_{15}$)alkoxycarbonyl, mono($C_1$–$C_{15}$)alkylaminocarbonyl, and di($C_1$–$C_{15}$)alkylaminocarbonyl radicals, wherein the alkylene radicals are optionally interrupted with at least one entity chosen from carbonyl functional groups and hetero atoms chosen from oxygen and nitrogen;
R' is chosen from a hydrogen atom, and $C_1$–$C_{15}$ alkyl, $C_1$–$C_{15}$ alkoxy, $C_1$–$C_{15}$ hydroxyalkoxy, ($C_1$–$C_{15}$)

alkoxy($C_1$–$C_{15}$)alkyl, $C_1$–$C_{15}$ monohydroxyalkyl, and $C_1$–$C_{15}$ polyhydroxyalkyl radicals; and n is an integer ranging from 1 to 4.

24. A ready-to-use cosmetic composition according to claim 23, wherein said at least one oxidizing agent is hydrogen peroxide.

25. A multi-compartment kit, comprising, at least one first compartment comprising at least one cosmetic composition for dyeing keratin fibers, comprising, in a medium that is suitable for dyeing, at least one secondary para-phenylenediamine compound chosen from compounds of formula (I) and the addition salts thereof:

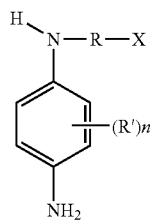

(I)

wherein:

X is a fluorine atom;

R is chosen from linear and branched $C_1$–$C_{10}$ alkylene radicals, which are unsubstituted or substituted with at least one entity chosen from halogens, and $C_1$–$C_{15}$ alkoxy, aryl, amino, mono($C_1$–$C_{15}$)alkylamino, di($C_1$–$C_{15}$)alkylamino, ($C_1$–$C_{15}$)alkylcarbonyl, carboxyl, amido, ($C_1$–$C_{15}$)alkoxycarbonyl, mono($C_1$–$C_{15}$)alkylaminocarbonyl, and di($C_1$–$C_{15}$)alkylaminocarbonyl radicals, wherein the alkylene radicals are optionally interrupted with at least one entity chosen from carbonyl functional groups and hetero atoms chosen from oxygen and nitrogen;

R' is chosen from a hydrogen atom, and $C_1$–$C_{15}$ alkyl, $C_1$–$C_{15}$ alkoxy, $C_1$–$C_{15}$ hydroxyalkoxy, ($C_1$–$C_{15}$) alkoxy($C_1$–$C_{15}$)alkyl, $C_1$–$C_{15}$ monohydroxyalkyl, and $C_1$–$C_{15}$ polyhydroxyalkyl radicals; and n is an integer ranging from 1 to 4; and at least one second compartment comprising at least one oxidizing agent.

\* \* \* \* \*

UNITED STATES PATENT AND TRADEMARK OFFICE
CERTIFICATE OF CORRECTION

PATENT NO. : 7,311,737 B2 Page 1 of 1
APPLICATION NO. : 11/066252
DATED : December 25, 2007
INVENTOR(S) : Eric Metais et al.

It is certified that error appears in the above-identified patent and that said Letters Patent is hereby corrected as shown below:

In claim 9, column 16, lines 60-61, "$(C_1\text{-}C_8)$alkoxy$(C_{1\text{-}8})$alkyl," should read --$(C_1\text{-}C_8)$alkoxy$(C_1\text{-}C_8)$alkyl,--.

Signed and Sealed this

Thirteenth Day of May, 2008

JON W. DUDAS
*Director of the United States Patent and Trademark Office*